(12) United States Patent
Scala et al.

(10) Patent No.: US 9,433,566 B2
(45) Date of Patent: Sep. 6, 2016

(54) SOAP BAR

(75) Inventors: Diana Scala, Hillsborough, NJ (US); Patricia Hall-Puzio, Succasunna, NJ (US); Michael Amoafo, Hillsborough, NJ (US); Perry Cai, Guangdong (CN); Jeffer Liang, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 20 days.

(21) Appl. No.: 14/379,537

(22) PCT Filed: Feb. 24, 2012

(86) PCT No.: PCT/CN2012/071560
§ 371 (c)(1),
(2), (4) Date: Aug. 19, 2014

(87) PCT Pub. No.: WO2013/123668
PCT Pub. Date: Aug. 29, 2013

(65) Prior Publication Data
US 2015/0024988 A1 Jan. 22, 2015

(51) Int. Cl.
| | | |
|---|---|---|
| *A61K 8/36* | (2006.01) |
| *C11D 9/18* | (2006.01) |
| *C11D 9/26* | (2006.01) |
| *A61K 8/02* | (2006.01) |
| *A61K 8/25* | (2006.01) |
| *A61K 8/34* | (2006.01) |
| *A61Q 19/10* | (2006.01) |
| *C11D 9/44* | (2006.01) |

(52) U.S. Cl.
CPC .............. *A61K 8/36* (2013.01); *A61K 8/0216* (2013.01); *A61K 8/25* (2013.01); *A61K 8/345* (2013.01); *A61Q 19/10* (2013.01); *C11D 9/18* (2013.01); *C11D 9/265* (2013.01); *C11D 9/267* (2013.01); *C11D 9/442* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 5,264,144 A | 11/1993 | Moroney et al. | |
| 6,143,704 A * | 11/2000 | Van Gunst et al. | 510/152 |
| 6,255,265 B1 * | 7/2001 | Van Gunst et al. | 510/152 |
| 6,534,687 B2 | 3/2003 | Schultz et al. | |
| 6,537,953 B2 | 3/2003 | Schultz et al. | |
| 6,537,954 B2 | 3/2003 | Schultz et al. | |
| 6,541,433 B2 | 4/2003 | Schultz et al. | |
| 6,589,923 B2 | 7/2003 | Lenuck et al. | |
| 6,630,432 B2 | 10/2003 | Farrell et al. | |
| 6,949,493 B1 | 9/2005 | Zhang et al. | |
| 7,442,674 B2 | 10/2008 | Polonka et al. | |
| 7,446,081 B2 | 11/2008 | Tsaur et al. | |
| 2007/0042920 A1 | 2/2007 | Schmit et al. | |
| 2008/0125340 A1 * | 5/2008 | Dail | 510/130 |
| 2008/0153728 A1 | 6/2008 | Dail et al. | |
| 2011/0077186 A1 * | 3/2011 | Lai et al. | 510/141 |

FOREIGN PATENT DOCUMENTS

| | | |
|---|---|---|
| CN | 1503837 | 6/2004 |
| CN | 101554357 | 10/2009 |
| EP | 0861317 B1 | 1/2000 |
| EP | 1581609 | 10/2005 |
| GB | 2459093 A | 10/2009 |
| RU | 2263709 | 3/2004 |
| WO | WO9709413 | 3/1997 |
| WO | WO 97/22684 | 6/1997 |
| WO | WO 00/22082 | 4/2000 |
| WO | WO2011073139 | 6/2011 |

OTHER PUBLICATIONS

International Search Report and the Written Opinion issued in International Application PCT/CN2012/071560 mailed Nov. 29, 2012. WO.
"Healthy Soap" Company: Reckitt Benckiser Brand: Dettol Active (Soap and bath products) Sold in China Oct. 2011.
Analysis of Cussons Carex Soap Bar, Sold in Thailand in 2009, nma.
Analysis of Cussons Imperial Leather Soap Bar, Sold in Thailand in 2009, nma.

* cited by examiner

*Primary Examiner* — Necholus Ogden, Jr.

(57) ABSTRACT

A surfactant free soap bar comprising soap, 0.1 to 2.5% by weight free fatty acid, 3 to 7% by weight talc, and 0.1 to 5% glycerin. The talc can be a macrocrystalline talc having $D90 \geq 20$ μm and optionally $D50 \geq 20$ μm or $D10 \geq 5$ μm. The combination provides increased skin feel and leaves skin looking less dry.

19 Claims, No Drawings

SOAP BAR

CROSS-REFERENCE TO RELATED PATENT APPLICATIONS

The present application is a U.S. national stage entry under 35 U.S.C. §371 of Patent Cooperation Treaty Patent Application No. PCT/CN2012/071560, filed Feb. 24, 2012, the entirety of which is incorporated herein by reference.

FIELD OF THE INVENTION

The present invention relates to soap bars.

BACKGROUND OF THE INVENTION

Soap bars contain soap made from salts of fatty acids. Soap bars are used for cleansing skin. When using soap bars, there is a desire for the soap to provide a desired skin feel and not dry the skin. It would be desirable to provide a soap bar that can leave skin not looking dry and looking moisturized.

BRIEF SUMMARY OF THE INVENTION

A surfactant free soap bar comprising soap, free fatty acid in an amount of 0.1 to 2.5% by weight of the bar, talc in an amount of 3 to 7% by weight of the bar, and glycerin in an amount of 0.1 to 5% by weight of the bar. The soap bar can also be used in a method to cleanse skin by cleansing with the soap bar. Also a use of 0.1 to 2.5% by weight free fatty acid, 3 to 7% by weight talc, and 0.1 to 5% glycerin in a soap bar for reducing dryness on skin or increasing fragrance perception.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The term surfactant free means that there is less than 0.5% by weight of anionic, nonionic, amphoteric, and zwitterionic surfactants total in the soap bar. While soap is an anionic surfactant, the term soap is not included in the exclusion of anionic surfactants. Also, the term surfactant free can also exclude cationic surfactants that are not present to provide conditioning or antibacterial effect. Some cationic surfactants can condition skin or provide an antibacterial effect. These types of materials can be included in the soap bar. In other embodiments, there is less than 0.4, less than 0.3, less than 0.2, less than 0.1, less than 0.05, less than 0.01, or no surfactant in the soap bar.

The soap can be made from typical fatty acids, such as $C_{12}$-$C_{20}$ fatty acids. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any base to form a soap. Typical bases include, but are not limited to, sodium hydroxide, potassium hydroxide, and triethanolamine.

The soap bar includes free fatty acid, which is present in acid form. The free fatty acids can be any of the above fatty acids that are used to make soap. The free fatty acid is present in the soap bar in an amount of 0.1 to 2.5% by weight of the bar. In other embodiments, the amount of free fatty acid is 0.1 to 2%, 0.1 to 1.5%, 0.1 to 1%, 0.5 to 2%, 0.5 to 1%, 1.2% or 1% by weight of the bar.

The soap bar includes talc. The talc is present in the soap bar in an amount of 3 to 7% by weight of the bar. In other embodiments, the amount of talc is 4 to 6%, 4.5 to 5.5% or 5% by weight of the bar. In certain embodiments, the talc is a macrocrystalline talc, which has large particle sizes. In certain embodiments, the talc has D90≥40 μm, optionally D90≥50 μm or D90≥60 μm. In other embodiments, the talc has D50≥20 μm, optionally D50≥25 μm. In another embodiment, the talc has D10≥5 μm. In another embodiment, the talc has D90≥50 μm and D50≥20 μm, optionally D90≥60 μm.

The soap bar also includes glycerin. The glycerin is present in an amount of 0.1 to 5% by weight of the soap bar. In other embodiments, glycerin is present in an amount of 0.1 to 3%, 0.1 to 2%, 0.1 to 1.5%, 0.1 to 1%, 0.5 to 2%, 0.5 to 1.5%, 0.7%, 1%, or 1.4% by weight of the bar.

Optionally, the soap bar can contain any other materials that can be added to soap bars. Examples include, but are not limited to, fillers, fragrances, colorants, pH agents, antibacterial actives, preservatives, deodorant actives, emollients, moisturizers, vitamins, and exfoliating agents.

The soap bar can leave skin feeling and looking more moisturized and less dry. Also, the perception of fragrance can be increased using the combination of free fatty acid, talc, and glycerin in the soap bar.

EXAMPLES

The following soap bars are prepared.

| Material | Example 1 (wt. %) | Comparative (wt. %) |
| --- | --- | --- |
| Free fatty acid | 2 | 5 |
| Talc | 5 | 5 |
| Glycerin | 2 | 2 |
| Soap and minors | Q.S. | Q.S. |

Note, the same talc is used in both bars. The talc is the macrocrystalline talc.

Ten panelists wash one forearm with Example 1 and the other forearm with the comparative soap bar Immediately after washing, the panelists are asked which soap was preferred. Seven out of ten preferred Example 1 with 2 weight % fatty acid compared to the 5 weight % fatty acid soap bars.

The following soap bars are prepared.

| Material | Example 2 (wt. %) | Comparative (wt. %) |
| --- | --- | --- |
| Free fatty acid | 2 | 2 |
| Talc | 5 | 5 |
| Glycerin | 2 | 2 |
| Soap and minors | Q.S. | Q.S. |

Note, Example 2 uses the macrocrystalline talc, and the comparative uses a standard talc that is not macrocrystalline.

Ten panelists wash one forearm with Example 2 and the other forearm with the comparative soap bar Immediately after washing, the panelists are asked which soap was preferred. Eight out of ten preferred Example 2 with the macrocrystalline talc.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A surfactant free soap bar comprising:
   a) soap,
   b) free fatty acid in an amount of 0.1 to 2.5% by weight of the bar,
   c) talc in an amount of 3 to 7% by weight of the bar, the talc having D90≥40 μm, and
   d) glycerin in an amount of 0.1 to 5% by weight of the bar.

2. The soap bar of claim 1, wherein the free fatty acid is present in an amount of 0.1 to 2% by weight of the bar.

3. The soap bar of claim 1, wherein the talc is present in an amount of 4 to 6% by weight of the bar.

4. The soap bar of claim 1, wherein the glycerin is present in an amount of 0.1 to 3% by weight of the bar.

5. The soap bar of claim 1, wherein the talc has D90≥50 μm and D50≥20 μm.

6. The soap bar of claim 1, wherein the composition comprises one of:
   a) 0.7% by weight glycerin, 1.2% by weight free fatty acid, and 5% by weight talc,
   b) 4.5% by weight glycerin, 1% by weight free fatty acid, and 5% by weight talc,
   c) 1.4% by weight glycerin, 1.2% by weight free fatty acid, and 5% by weight talc, or
   d) 1% by weight glycerin, 1% by weight free fatty acid, and 5% by weight talc.

7. A method for cleansing skin comprising cleansing skin with the soap bar of claim 1.

8. A surfactant free soap bar comprising:
   a) soap,
   b) free fatty acid in an amount of 0.1 to 2.5% by weight of the bar,
   c) talc in an amount of 3 to 7% by weight of the bar, the talc having D50≥20 μm and
   d) glycerin in an amount of 0.1 to 5% by weight of the bar.

9. The soap bar of claim 8, wherein the free fatty acid is present in an amount of 0.1 to 2% by weight of the bar.

10. The soap bar of claim 8, wherein the talc is present in an amount of 4 to 6% by weight of the bar.

11. The soap bar of claim 8, wherein the glycerin is present in an amount of 0.1 to 3% by weight of the bar.

12. The soap bar of claim 8, wherein the composition comprises one of:
    a) 0.7% by weight glycerin, 1.2% by weight free fatty acid, and 5% by weight talc,
    b) 4.5% by weight glycerin, 1% by weight free fatty acid, and 5% by weight talc,
    c) 1.4% by weight glycerin, 1.2% by weight free fatty acid, and 5% by weight talc, or
    d) 1% by weight glycerin, 1% by weight free fatty acid, and 5% by weight talc.

13. A method for cleansing skin comprising cleansing skin with the soap bar of claim 8.

14. A surfactant free soap bar comprising:
    a) soap,
    b) free fatty acid in an amount of 0.1 to 2.5% by weight of the bar,
    c) talc in an amount of 3 to 7% by weight of the bar, the talc having D10≥5 μm, and
    d) glycerin in an amount of 0.1 to 5% by weight of the bar.

15. The soap bar of claim 14, wherein the free fatty acid is present in an amount of 0.1 to 2% by weight of the bar.

16. The soap bar of claim 14, wherein the talc is present in an amount of 4 to 6% by weight of the bar.

17. The soap bar of claim 14, wherein the glycerin is present in an amount of 0.1 to 3% by weight of the bar.

18. The soap bar of claim 14, wherein the composition comprises one of:
    a) 0.7% by weight glycerin, 1.2% by weight free fatty acid, and 5% by weight talc,
    b) 4.5% by weight glycerin, 1% by weight free fatty acid, and 5% by weight talc,
    c) 1.4% by weight glycerin, 1.2% by weight free fatty acid, and 5% by weight talc, or
    d) 1% by weight glycerin, 1% by weight free fatty acid, and 5% by weight talc.

19. A method for cleansing skin comprising cleansing skin with the soap bar of claim 14.

* * * * *